United States Patent [19]

Schelbeck

[11] Plant 5,169

[45] Jan. 3, 1984

[54] BEGONIA PLANT NAMED CONNIE

[75] Inventor: Erland V. Schelbeck, Odense, Denmark

[73] Assignee: L. Daehnfeldt Ltd., Odense, Denmark

[21] Appl. No.: 420,500

[22] Filed: Sep. 20, 1982

[51] Int. Cl.[3] ..... A01H 5/00

[52] U.S. Cl. ..... Plt./68

[58] Field of Search ..... Plt./68

*Primary Examiner*—Robert E. Bagwill

*Attorney, Agent, or Firm*—Schwartz, Jeffery, Schwaab, Mack, Blumenthal & Koch

[57] ABSTRACT

A begonia hybrid named Connie having rose-red, double sterile flowers up to 5 cm. in diameter, medium size slightly convex dark green glabrous leaves, upright growth, and having excellent flowering and keeping qualities for year round production in various size containers.

1 Drawing Figure

The present invention relates to a new and distinct cultivar of begonia plant, botanically known as *hiemalis begonia* (*Fotsch*), and referred to by the cultivar name Connie.

The new cultivar was discovered by me in Odense, Denmark as a seedling from a controlled crossing of my tuberhybrida seedling P-199 as the seed parent with species *b. Socotrana* as the pollen parent. Asexual reproduction by stem and leaf cuttings by me in Odense, Denmark has reproduced the unique features of the new cultivar through successive propagations.

The following characteristics distinguish the new begonia from both its parent and other begonias commercially known and used in the floriculture industry:

1. My new cultivar has smaller leaves, shorter compact growth and year round flowering compared to the tuberous seed parent P-199 which drops its flowers during the shortened days of late autumn and winter.

2. The foliage of my new cultivar is darker green in comparison to the light green foliage of the species pollen parent *Socotrana.*

3. The flowers are double rose-red while the flowers of *Socotrana* are single (4 tepals) and light pink. In comparison to my new cultivar Dorthe, disclosed in my pending application Ser. No. 420,521, filed Sept. 20, 1982, Connie's flowers have a tint of blue giving a rose-red coloration whereas Dorthe's flowers are true red.

4. The racemes are tightly clustered in the early flowering stages and may have up to 8–10 flowers in the inflorescence.

5. In comparison to Riegers Aphrodite Cherry Red (U.S. Plant Pat. No. 3,319), the flowers of Connie are more double, have better keeping qualities in dark weather, and are similar in color but brighter in tone than Aphrodite Cherry Red.

6. Riegers Aphrodite types are difficult to propagate by leaf cuttings but my new cultivar propagates by leaf cuttings quite readily without problems. The free branching habit also allows stem or tip cutting propagation.

7. The excellent keeping qualities of the flowers allows growers to use this cultivar in year round flowering, especially for hanging baskets in the United States.

8. Flowering response is nearly indeterminant. However, shortening the day length during periods of long days hastens and increases the flowering response.

9. The nearly rounded dark green foliage gives a pleasing contrast to the rose-red flowers.

10. Connie responds well to the growth regulators Cycocel and A-Rest, and thus can be produced in small 10 cm. pots, 15 cm. pots and hanging baskets.

The accompanying colored photograph taken in June 1982 illustrates in perspective the overall appearance of the new cultivar, grown in a 15 cm. pot from leaf cuttings, and showing the colors as true as it is reasonably possible to obtain in a colored reproduction of this type.

The following is a detailed description of my new begonia cultivar based on plants produced under commercial practices in Odense, Denmark and Ashtabula, Ohio. Color references are made to The Royal Horticultural Society Colour Chart except where general color terms of ordinary dictionary significance are used.

PARENTAGE

A controlled cross of begonia tuberous hybrida P-199 and *b. Socotrana.*

PROPAGATION (A) Type cutting: Leaf cuttings.

(B) Time to root: 15° at 21° C. summer, 24° at 21° C. winter.

(C) Rooting habit: Rooting is quite uniform, dendritic and fibrous.

(D) Time for shoot development: Total time from sticking the leaf cutting to adventitious shoots 5–6 cm. in length is 65 days in summer to 80 days in winter.

PLANT DESCRIPTION (A) Form: Compact, rounded, close internoded, vigorous, self supporting, herbaceous.

(B) Habit of growth: Rapid, upright, high degree of self branching.

(C) Foliage: Leaves simple, alternate, borne on vigorous petioles up to 5 mm. in diameter.

(1) *Size.*—Average size is 9–10 cm. If plant develops with fewer shoots than illustrated, leaves may be 10–12 cm; conversely only 5–6 cm.

(2) *Shape.*—Ovate to nearly orbicular with slightly overlapping lobes and slightly convex.

(3) *Texture.*—Leaf is firm to crisp, top side glabrous, underside rugose.

(4) *Margin.*—Serrate to crenulate.

(5) *Color.*—Young foliage, top side yellow green 147A; under side yellow green 148B, slight reddening; Mature foliage, top side darker than 147A, toward green 135A, underside green 138A and without red coloration.

(6) *Venation.*—Palmate.

FLOWERING DESCRIPTION (A) Flowering habits: Flowering in racemes with inflorescence having up to 10–12 flowers in bloom at same time, as illustrated. Flowering continues more or less indefinitely.

(B) Natural flowering season: Will flower in all seasons, including summer, without controlling day length. More uniform and abundant flowering does occur with increased maturity of plant and reducing day length to 12 hours.

(C) Flower bud description: Flat and nearly circular; buds begin to open when approximately 2.5 cm. in diameter.

(D) Flowers born: On sturdy pedicels within the form of the raceme.

(E) Quantity: Dependent on the number of shoots that are available for flowering. The plant illustrated had approximately 75 blossoms and would be considered highly floriferous as other buds were developing at same time.

(F) Tepals:

(1) *Shape.*—Flat and nearly circular.

(2) *Color.*—Top side in winter when opening, red 45B to 46B with blue tinging; summer top red 45C, fading to red 51A on oldest tepals in summer; under side red 48A but darker with high light to red 50A (3) *Number of tepals.*—Flowers can be very double with up to 35–40 tepals. Quite often flowers appear to be faciated and present multiple centers, thus increasing petal count and size.

(4) *Size of tepals.*—Basal from 35 mm. interior tepals 15 mm.

(6) *Flower size.*—Up to 5 cm. in diameter.

(G) Reproductive organs: None, cultivar is sterile triploid.

DISEASE RESISTANCE

Connie appears to have above average resistance to powdery mildew when grown in the presence of mildew infected begonias.

I claim:

1. A new and distinct cultivar of begonia known by the cultivar name Connie, as described and illustrated, and particularly characterized by its double rose-red flowers which are up to 5 cm. in diameter; medium size dark green glabrous leaves; upright and compact growth habit; ease of propagation; excellent and continuous flowering year round, and excellent keeping qualities.

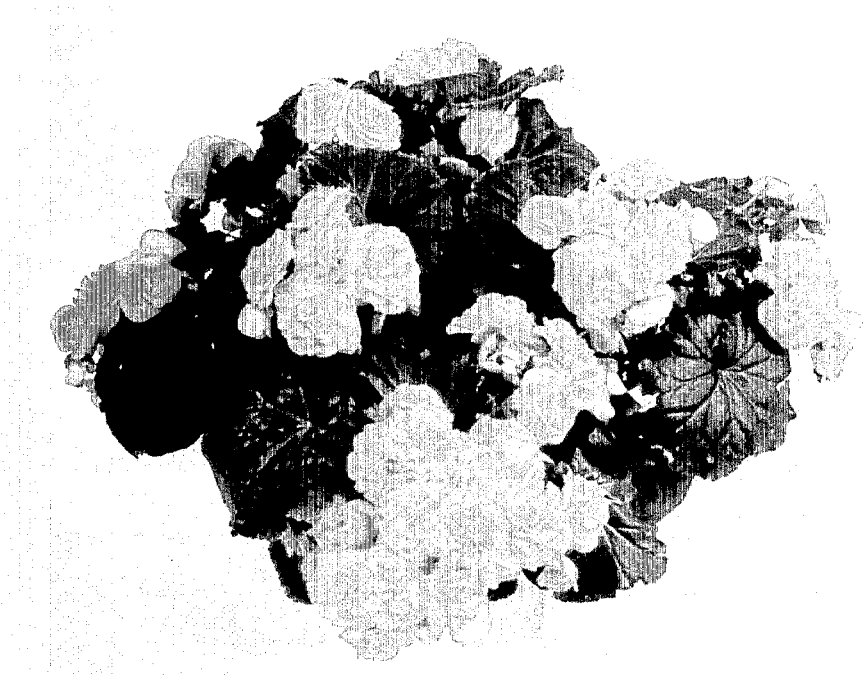

* * * * *